US011311477B2

(12) United States Patent
Lee et al.

(10) Patent No.: US 11,311,477 B2
(45) Date of Patent: Apr. 26, 2022

(54) OPHTHALMIC PREPARATIONS

(71) Applicant: SGN Nanopharma Inc., Tampa, FL (US)

(72) Inventors: Robert Lee, Malvern, PA (US); Dinesh Shenoy, Malvern, PA (US)

(73) Assignee: SGN NANOPHARMA INC., Tampa, FL (US)

( * ) Notice: Subject to any disclaimer, the term of this patent is extended or adjusted under 35 U.S.C. 154(b) by 5 days.

(21) Appl. No.: 16/183,593

(22) Filed: Nov. 7, 2018

(65) Prior Publication Data

US 2019/0070106 A1 Mar. 7, 2019

Related U.S. Application Data

(60) Division of application No. 12/007,902, filed on Jan. 16, 2008, now Pat. No. 10,137,083, which is a continuation-in-part of application No. 11/714,274, filed on Mar. 6, 2007.

(60) Provisional application No. 60/837,294, filed on Aug. 14, 2006, provisional application No. 60/779,420, filed on Mar. 7, 2006.

(51) Int. Cl.
| | |
|---|---|
| *A61K 9/107* | (2006.01) |
| *A61K 38/13* | (2006.01) |
| *A61K 47/10* | (2017.01) |
| *A61K 47/18* | (2017.01) |
| *A61K 47/26* | (2006.01) |
| *A61K 47/44* | (2017.01) |
| *A61K 9/00* | (2006.01) |

(52) U.S. Cl.
CPC .......... *A61K 9/0048* (2013.01); *A61K 9/1075* (2013.01); *A61K 38/13* (2013.01); *A61K 47/10* (2013.01); *A61K 47/186* (2013.01); *A61K 47/26* (2013.01); *A61K 47/44* (2013.01)

(58) Field of Classification Search
None
See application file for complete search history.

(56) References Cited

U.S. PATENT DOCUMENTS

| | | |
|---|---|---|
| 4,108,985 A | 8/1978 | Ruegger et al. |
| 4,210,581 A | 7/1980 | Ruegger et al. |
| 4,220,641 A | 9/1980 | Traber et al. |
| 4,384,996 A | 5/1983 | Bollinger et al. |
| 4,703,033 A | 10/1987 | Seebach |
| 4,764,503 A | 8/1988 | Wenger |
| 5,145,684 A | 9/1992 | Liversidge et al. |
| 5,474,979 A | 12/1995 | Ding et al. |
| 5,496,811 A * | 3/1996 | Aviv ................... A61K 9/0048 514/78 |
| 5,510,118 A | 4/1996 | Bosch et al. |
| 5,518,187 A | 5/1996 | Bruno et al. |
| 5,629,021 A | 5/1997 | Wright |
| 5,660,858 A * | 8/1997 | Parikh ................... A61K 38/13 424/450 |
| 5,698,219 A | 12/1997 | Valdivia et al. |
| 5,718,388 A | 2/1998 | Czekai et al. |
| 5,862,999 A | 1/1999 | Czekai et al. |
| 5,965,160 A | 10/1999 | Benita et al. |
| 6,063,762 A | 5/2000 | Hong et al. |
| 6,113,921 A | 9/2000 | Friedman et al. |
| 6,254,860 B1 | 7/2001 | Garst |
| 6,267,989 B1 | 7/2001 | Liversidge et al. |
| 6,350,442 B2 | 2/2002 | Garst |
| 6,406,718 B1 | 6/2002 | Cooper |
| 2001/0007663 A1* | 7/2001 | Von Corswant ..... A61K 9/1075 424/400 |
| 2003/0087953 A1 | 5/2003 | Palepu et al. |
| 2003/0143250 A1 | 7/2003 | Hauer et al. |
| 2003/0171264 A1 | 9/2003 | Naicker et al. |
| 2004/0006012 A1 | 1/2004 | Cottens et al. |
| 2004/0023885 A1* | 2/2004 | Brand ................ A61K 2300/00 514/6.9 |
| 2005/0059583 A1* | 3/2005 | Acheampong ......... A61K 47/02 514/20.5 |
| 2005/0208083 A1 | 9/2005 | Annis |
| 2007/0248645 A1 | 10/2007 | Bague et al. |
| 2007/0264349 A1 | 11/2007 | Lee et al. |
| 2010/0003330 A1 | 1/2010 | Baker, Jr. et al. |
| 2019/0390011 A1* | 12/2019 | Nagelsdiek .............. C09D 7/65 |

FOREIGN PATENT DOCUMENTS

| | | | |
|---|---|---|---|
| CN | 1686533 A | * | 10/2005 |
| CN | 102492092 B | * | 5/2014 |
| GB | 2 206 119 | | 12/1988 |
| WO | WO1996/23409 | | 8/1996 |
| WO | WO-97/14407 A1 | | 4/1997 |
| WO | WO2003/032949 | | 4/2003 |
| WO | WO2003/053405 | | 7/2003 |
| WO | WO2006/050838 A2 | | 5/2006 |

OTHER PUBLICATIONS

Kronemyer, Cyclosporine eye drop is effective and safe for dry eye, studies show, Ocular Surgery News U.S. Edition, Jun. 1, 2000, 3 pages.*
Stevenson et al., Efficacy and safety of cyclosporin A ophthalmic emulsion in the treatment of moderate-to-severe dry eye disease: a dose-ranging, randomized trial. The Cyclosporin A Phase 2 Study Group, Ophthalmology. May 2000;107(5):967-74, 2 pages, Abstract only.*
Wollenweber et al., Adsorption of hydroxypropyl methylcellulose at the liquid/liquid interface and the effect on emulsion stability, Colloids and Surfaces A:Physicochemical and Engineering Aspects,vol. 172,Iss 1-3, Oct. 25, 2000, p. 91-101, printed from https://www.infona.pl, 2 pages, Abstract only.*
Rowe et al., Glycerin, Handbook of Pharmaceutical Excipients, 2003, Pharmacuetical Press, 257-259.*
Office Action cited in related U.S. Appl. No. 11/714,274, dated Oct. 20, 2010.

(Continued)

*Primary Examiner* — Gigi G Huang
(74) *Attorney, Agent, or Firm* — Foley & Lardner LLP (57) ABSTRACT

The present invention provides ophthalmic formulations containing cyclosporine, methods for preparing the formulation, and methods for using the formulation.

21 Claims, 5 Drawing Sheets

(56) References Cited

OTHER PUBLICATIONS

Office Action cited in related U.S. Appl. No. 11/714,274, dated Mar. 1, 2011.
Office Action issued in related U.S. Appl. No. 11/714,274, dated Apr. 29, 2014.
Office Action issued in related U.S. Appl. No. 11/714,274, dated Aug. 11, 2011.
Office Action issued in related U.S. Appl. No. 11/714,274, dated Nov. 10, 2014.
Final Office Action issued in related U.S. Appl. No. 11/714,274, dated Jun. 13, 2016.
Non-Final Office Action issued in related U.S. Appl. No. 11/714,274, dated Mar. 15, 2017.
Office Action issued in related U.S. Appl. No. 11/714,274, dated Sep. 27, 2017.
Lallemand et al., "Cyclosporine A Delivery to the Eye: A Pharmaceutica Challenge," *European Journal of Pharm. and Biopharm.* 56, pp. 307-318 (2003).
Kunert et al., "Analysis of Topical Cyclosporine Treatment of Patients with Dry Eye Syndrome," Clinical Sciences, pp. 1489-1496 (2000).
Kibbe, "Benzalkonium Chloride," Handbook of Pharmaceutical Excipients, pp. 33-35 (2000).
Cross et al., "Clinical and Economic Implications of Topical Cyclosporin A for the Treatment of Dry Eye," *Managed Care Interface*, pp. 44-49 (2002).
Prummel et al., "Prednisone and Cyclosporine in the Treatment of Severe Graves' Ophthalmophathy," vol. 321, No. 20, pp. 1353-1359.
Reinhard et al., "Systemic Cyclosporin A Prophylaxis after Keratoplasties with an Elevated Risk for Immune Reactions as the only Elevated Risk Factor," *Ophthalmologe*, pp. 496-500 (1997), [Abstract p. 497].
Georganas et al., "Relapsing Wegener's Granulomatosis: Successful Treatment with Cyclosporin-A," *Clinical Rheumatology*, pp. 189-192 (1996).
Masuda et al., "Double-Masked Trial of Cyclosporin Versus Colchicine and Long-Term Open Study of Cyclosporin in Behcet's Disease," *The Lancet*, pp. 1093-1096 (1989).
Nussenblatt et al., "Randomized, Double-Masked Study of Cyclosporine Compared to Prednisolone in the Treatment of Endogenous Uveitis," *American Journ. of Ophthalmology*, 112, pp. 138-146 (1991).
Kunert et al., "Goblet Cell Numbers and Epithelial Proliferation in the Conjunctiva of Patients with Dry Eye Syndrome Treated with Cyclosporine," *Laboratory Sciences*, pp. 330-337, p. 1099 correction page (2002).

Theander et al., "Cyclosporin Ophthalmic Emulsion," 4 pages (1999).
Office Action cited in related U.S. Appl. No. 11/714,274, dated Feb. 22, 2010.
International Preliminary Report on Patentability for International Patent Application No. PCT/US2007/005562, dated Sep. 9, 2008, 7 pgs.
International Search Report for related International Application No. PCT/US2009/031111 dated Apr. 21, 2009.
Written Opinion of the International Searching Authority for related International Application No. PCT/US2009/031111 dated Apr. 21, 2009.
Hendrickson et al., Remington: The Science and Practice of Pharmacy—Solutions, Emulsions, Suspensions, and Extracts; Preservatives 2005, pp. 747-749 (2005).
Office Action cited in related U.S. Appl. No. 11/714,274, dated Jan. 14, 2019.
Office Action issued in co-pending U.S. Appl. No. 11/714,274, dated Sep. 5, 2019.
U.S. Appl. No. 10/137,083, filed Nov. 27, 2018, Lee et al.
Office Action issued in co-pending U.S. Appl. No. 16/183,562, dated Jun. 26, 2019.
Office Action issued in co-pending U.S. Appl. No. 16/183,562, dated Dec. 16, 2019.
Beauchamp et al. "A Critical Review of the Toxicology of Glutaraldehyde," Critical Reviews in Toxicology, vol. 22, 1992, pp. 143-174 [Abstract Only].
Hansen, "KS Occupational Dermatoses in Hospital Cleaning Women," Contact Dermatitis, vol. 9, 1983, pp. 343-351 [Abstract Only].
Non-Final Office Action on U.S. Appl. No. 16/183,562 dated Jul. 10, 2020 (15 pages).
Physicians Desk Reference, 56th Ed., 2002, pp. 513-516.
Russell et al., "Do Antiseptics and Disinfectants Select for Antibiotic Resistance," Journal of Medicinal Microbiology, vol. 48, 1999, pp. 613-615.
Rutala, "APIC Guideline for Selection and Use of Disinfectants," Amer. J., vol. 24, 1996, pp. 313-342.
Office Action issued in co-pending U.S. Appl. No. 16/183,562, dated Jan. 26, 2021.
Office Action issued in co-pending U.S. Appl. No. 11/714,274, dated Jan. 6, 2021.
Notice of Allowance issued in U.S. Appl. No. 16/183,562, dated Sep. 15, 2021.
Office Action issued in co-pending U.S. Appl. No. 11/714,274, dated Jul. 14, 2021.

\* cited by examiner

OPHTHALMIC PREPARATIONS

CROSS-REFERENCE TO RELATED APPLICATIONS

This application is a divisional of U.S. patent application Ser. No. 12/007,902, filed Jan. 16, 2008, which is a continuation-in-part of U.S. patent application Ser. No. 11/714,274, filed Mar. 6, 2007, which claims priority from U.S. Provisional Application Nos. 60/779,420, filed Mar. 7, 2006, and 60/837,294, filed Aug. 14, 2006. The contents of these applications are hereby incorporated by reference in their entirety.

FIELD OF THE INVENTION

The invention is directed to ophthalmic formulations, methods for preparing the ophthalmic formulation, and methods of using the ophthalmic formulation.

BACKGROUND

Most ocular medications may be administered topically to treat surface as well as intraocular disorders. This route is often preferred for the management of various pathological diseases that affect the anterior chamber of the eye, for two main reasons: (1) it is more conveniently administered and (2) provides a higher ratio of ocular to systemic drug levels. To be administered topically and to achieve the necessary patient compliance, the medication must present a good local tolerance.

Cyclosporine is a known immunosuppressant, which acts by reducing inflammatory cells such as activated lymphocytes in the conjunctiva (Kunert et al., *Arch Ophthalmol.*, 118:1489-96, 2000) or by increasing the number of mucin secreting goblet cells (Kunert et al., *Arch Ophthalmol.*, 120:330-7, 2002). Over the years, Cyclosporine A (CsA) has been evaluated for numerous potential applications in ophthalmology.

New developments in the topical delivery of CsA can be divided in two general areas of research: new delivery systems, such as solutions, ointments, colloidal carriers and drug impregnated contact lenses, and chemical modifications of drugs or prodrugs.

At the present time, only one ophthalmic formulation of CsA is commercially available, which is currently marketed as Restasis®. The extensive literature on the delivery of CsA to the eye (Lallemand et al., *European Journal of Pharmaceutics and Biopharmaceutics* 56: 307-318, 2003; Nussenblatt et al., *Am. J. Ophthalmol.* 112: 138-146, 1991; Masuda et al., *Lancet* 1: 1093-1096, 1989; Georganas et al., *Clin. Rheumatol.* 15: 189-192, 1996; Prummel et al., *N. Engl. J. Med.* 321: 1353-1359, 1989; Reinhard et al., *Ophthalmologe* 94: 496-500, 1997) reflects the great medical interest and the pharmaco-economical aspects of this challenge. Despite a poor intraocular penetration, topical CsA has been successfully used in a variety of immune-mediated ocular surface phenomena such as vernal conjunctivitis, dry eye syndrome and the prevention of corneal allograft rejection. For example, Cross et al. reported that topical cyclosporine eye drop therapy not only improved the signs and symptoms of dry eye disease, but also resulted in high patient satisfaction, fewer patients with chronic dry eye visiting the ophthalmologist, and less ancillary drug use (*Manag. Care Interface* 2002; 15:44-49).

One obstacle to preparing an ophthalmic CsA formulation is that CsA cannot be prepared in formulations based on the commonly used aqueous ophthalmic vehicles because of both its hydrophobicity (log P=3.0) and its extremely low aqueous solubility at 6.6 mg/ml. Therefore, in most studies, CsA was dissolved and administered in vegetable oils. However, these media are poorly tolerated, resulting in relatively low ocular availability. Also, formulations prepared in these media have short shelf lives.

Oil-in-water emulsions are particularly useful in the delivery of lipophilic drugs. In vivo data from early studies confirmed that emulsions could be effective topical ophthalmic drug delivery systems, with a potential for sustained drug release.

The product currently on the market, Restasis®, is packaged in single unit doses to avoid microbial contamination because it does not contain any preservatives. It would be highly desired to have a preparation to be dispensed in a multi-dose container.

Therefore, there is a need for an ideal topical ocular formulation of CsA, which fulfills several requirements: (1) the formulation must be well tolerated, or non-irritating to the eye, (2) the formulation must be easy to administer, (3) the formulation ideally has an increased CsA residence time in the eye, (4) systemic absorption of the formulation should be avoided because the toxic CsA concentration in blood is above 300 ng/ml, (5) the formulation should have a long shelf life, and (6) the formulation should be easily manufactured.

The present invention satisfies the needs in the field by providing stable, non-irritating emulsion formulations of CsA suitable for ophthalmic application, and methods for preparing and using the formulations.

SUMMARY

One aspect of the invention relates to an ophthalmic formulation comprising: (a) cyclosporine or a derivative thereof, (b) at lest one solvent, (c) at least one oil, (d) at least one surfactant, (e) at least one preservative, and (f) water or buffer. In one embodiment, the cyclosporine (Cs) or a derivative thereof can be present in (a) a solid nanoparticulate state; (b) a solid microparticulate state; (c) solubilized; or (d) any combination thereof. An exemplary cyclosporine useful in the invention is cyclosporine A (CsA).

In one embodiment of the invention, the ophthalmic formulation further comprises a viscosity modifier, such as a cellulose derivative, a polysaccharide or a synthetic polymer.

In another embodiment of the invention, the formulation is a mixture of particles of cyclosporine or a derivative thereof suspended in emulsion droplets and sterically stabilized particulate cyclosporine or a derivative thereof in water or buffer.

Another aspect of the invention is directed to an opthalmic cyclosporine composition which is cationic. The cationic nature of the formulation results in an increased residency in the eye, producing a more effective dosage form. The cationic nature of the dosage form can result, for example, from the inclusion of a cationic preservative.

In yet another embodiment, the formulation comprises globules of oil comprising dissolved cyclosporine or a derivative thereof. The globules can have a diameter, for example, of less than about 10 microns, less than about 9 micros, less than about 8 microns, less than about 7 microns, less than about 6 microns, less than about 5 microns, less than about 4 microns, less than about 3 microns, less than about 2 microns, less than about 1000 nm, less than about 900 nm, less than about 800 nm, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm.

In some embodiments, the oil is selected from the group consisting of, but not limited to, sweet almond oil, apricot seed oil, borage oil, canola oil, coconut oil, corn oil, cotton seed oil, fish oil, jojoba bean oil, lard oil, boiled linseed oil, Macadamia nut oil, medium chain triglycerides (Crodamol GTCC), mineral oil, olive oil, peanut oil, safflower oil, sesame oil, soybean oil, squalene, sunflower seed oil, tricaprylin (1,2,3-trioctanoyl glycerol), and wheat germ oil.

In other embodiments, the solvent is selected from the group consisting of, but not limited to, isopropyl myristate, triacetin, N-methyl pyrrolidinone, aliphatic and aromatic alcohols, ethanol, dimethyl sulfoxide, dimethyl acetamide, ethoxydiglycol, polyethylene glycols, and propylene glycol. Other examples of useful solvents are long-chain alcohols. Ethanol is an example of a preferred alcohol that may be used in the present invention.

In further embodiments, the surfactant is selected from the group consisting of, but not limited to, sorbitan esters (such as Span or Arlacel), glycerol esters (such as glycerin monostearate), polyethylene glycol esters (such as polyethylene glycol stearate), block polymers (such as Pluronicst®), acrylic polymers (such as Pemulen®), ethoxylated fatty esters (such as Cremophor® RH-40), ethoxylated alcohols (such as Brij®), ethoxylated fatty acids (such as Tween or Tween 20), monoglycerides, silicon based surfactants and polysorbates. In a preferred embodiment, the surfactant is Polysorbate 80.

In one embodiment of the invention, the ophthalmic formulations of the invention have anti-microbial properties. In some embodiments, the formulation comprises a preservative suitable for opthalmic administration. Examples of such a preservative include, but are not limited to, quaternary ammonium compounds, such as cetyltrimethylammonium bromide, cetylpyridinium chloride, benzethonium chloride, and benzalkonium chloride. Preferably, the preservative is benzalkonium chloride.

In a preferred embodiment, the ophthalmic formulation comprises: (a) cyclosporine A, (b) ethanol, (c) medium chain triglycerides, (d) Polysorbate 80, (e) benzalkonium chloride, and (f) phosphate buffer.

Another aspect of the invention is directed to a method for preparing particles of Cs or a derivative thereof. The method comprises: (a) forming an emulsion base by suspending cyclosporine or a derivative thereof in a mixture of oil, solvent, surfactant, preservative, and water or buffer, and (b) homogenizing or vigorously stirring the emulsion base, wherein the resultant composition is a mixture of particles of cyclosporine or a derivative thereof suspended in emulsion droplets and sterically stabilized microcrystalline or nanoparticulate cyclosporine or a derivative thereof in the media. Optionally, the emulsion base of step (a) further comprises a viscosity modifier, such as a cellulose derivative, a polysaccharide or a synthetic polymer. In one embodiment, the particles of cyclosporine or a derivative thereof have a diameter of less than about 10 microns, less than about 9 microns, less than about 8 microns, less than about 7 microns, less than about 6 microns, less than about 5 microns, less than about 4 microns, less than about 3 microns, less than about 2 microns, less than about 1 micron, or even smaller in size. In another embodiment, the homogenizing step is performed via a high-pressure system at 1,000 to 40,000 psi.

Another aspect of the invention is directed to a method for preparing particles of Cs or a derivative thereof, comprising: (a) dissolving cyclosporine or a derivative thereof in a mixture of oil, solvent, and surfactant to form an emulsion pre-mix, (b) adding preservative, and water or buffer to the emulsion pre-mix, and (c) homogenizing or vigorously stirring the mixture, whereby cyclosporine or a derivative thereof is precipitated into particles. Optionally, the mixture of step (a) or that of step (b) further comprises a viscosity modifier, such as a cellulose derivative, a polysaccharide or a synthetic polymer. In one embodiment, the diameter of the particles of cyclosporine or a derivative thereof is less than about 10 microns, less than about 9 microns, less than about 8 microns, less than about 7 microns, less than about 6 microns, less than about 5 microns, less than about 4 microns, less than about 3 microns, less than about 2 microns, or less than about 1 micron. In another embodiment, the homogenizing step is performed via a high-pressure system at 1,000 to 40,000 psi.

In one embodiment, the particles of cyclosporine or a derivative thereof, droplets comprising cyclosporine or a derivative thereof, or a combination thereof, have a mean particle size of less than about 10 microns, less than about 9 microns, less than about 8 microns, less than about 7 microns, less than about 6 microns, less than about 5 microns, less than about 4 microns, less than about 3 microns, less than about 2900 nm, less than about 2800 nm, less than about 2700 nm, less than about 2600 nm, less than about 2500 nm, less than about 2400 nm, less than about 2300 nm, less than about 2200 nm, less than about 2100 nm, less than about 2000 nm, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 200 nm, or less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm. Preferably, the particles of cyclosporine or a derivative thereof, droplets comprising cyclosporine or a derivative thereof, or a combination thereof have a mean particle size of less than about 3 microns in diameter.

In a related aspect, the invention provides a method of treating a subject suffers from a condition, such as an aqueous deficient dry-eye state, phacoanaphylaxis endophthalmitis, uveitis, keratoconjunctivitis, allergic eye disorders, or immune-modulated eye diseases. The method comprises administering a therapeutically effective amount of the CsA formulations of the invention to the eye of a subject in need.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION

A. Overview of the Invention

The invention relates to ophthalmic formulations comprising cyclosporine or a derivative thereof and methods of making and using the same. One aspect of the present invention is directed to an ophthalmic formulation comprising: (a) cyclosporine or a derivative thereof, (b) at lest one solvent, (c) at least one oil, (d) at least one surfactant, (e) at least one preservative, and (f) water or buffer. In one embodiment, the cyclosporine (Cs) or a derivative thereof can be present in (a) a solid nanoparticulate state; (b) a solid microparticulate state; (c) solubilized; or (d) any combination thereof. In another embodiment, the ophthalmic formulation further comprises a viscosity modifier, such as a cellulose derivative, a polysaccharide or a synthetic polymer.

The cyclosporine can be, for example, cyclosporine A, and the cyclosporine or a derivative thereof can be in an amorphous form, semi-amorphous form, crystalline form, semi-crystalline form, or any combination thereof.

In one embodiment of the invention, the opthalmic cyclosporine composition is cationic. The cationic nature of the formulation can result in an increased residency in the eye, producing a more effective dosage form. Moreover, the increased residency in the eye can result in a need for fewer applications, a decreased drug dosage for effectiveness, and increased patient compliance (as fewer applications are desirable to patients). The cationic nature of the dosage form can result, for example, from the inclusion of a cationic preservative. An exemplary cationic preservative is benzalkonium chloride.

In another embodiment of the invention, the formulation is a mixture of particles of cyclosporine or a derivative thereof suspended in emulsion droplets and sterically stabilized particulate cyclosporine or a derivative thereof in water or buffer.

Another aspect of the invention encompasses a method of making a tri-phasic composition comprising a lipophilic phase, water or a buffer, and particulate cyclosporine or a derivative thereof. The invention also encompasses compositions comprising an oil phase that has at least one oil, at least one solvent, and a surfactant for cyclosporine or a derivative thereof. Two specific methods of making the composition of the invention are described. In the first method ("Route I"), cyclosporine or a derivative thereof is milled in an emulsion base. This method requires that cyclosporine or a derivative thereof is poorly soluble or insoluble in all phases of the oil phase/lipophilic phase and the water or buffer. In the second method ("Route II"), simultaneous milling and precipitation of cyclosporine or a derivative thereof in an emulsion base is observed. The second method requires that cyclosporine or a derivative thereof is soluble or partially soluble in one or more phases of the emulsion base.

One benefit of the invention is to provide a method applicable to cyclosporine or a derivative thereof, which is poorly water-soluble, since the conventional method, such as wet milling, is not effective. Another benefit of the invention is that it does not require grinding media or specialized grinding process or equipment. The use of such grinding media can add cost and complexity to a particle size reduction process for cyclosporine.

For Route I, cyclosporine or a derivative thereof is first suspended in a mixture of a non-miscible liquid, such as an oil, solvent, preservative and water or buffer, to form an emulsion base, followed by homogenization or vigorous stirring of the emulsion base. Optionally, the emulsion base further comprises a viscosity modifier, such as a cellulose derivative, a polysaccharide or a synthetic polymer. Nanoparticles can be produced with reciprocating syringe instrumentation, continuous flow instrumentation, or high speed mixing equipment. High velocity homogenization or vigorous stirring, producing forces of high shear and cavitation, are preferred. High shear processes are preferred as low shear processes can result in larger particle sizes of cyclosporine or a derivative thereof. The resultant composition is a composite mixture of cyclosporine or a derivative thereof suspended in the emulsion droplet (nanoemulsion fraction) and sterically stabilized micro-/nano-crystalline cyclosporine or a derivative thereof in the media. This tri-phasic system comprises particulate cyclosporine or a derivative thereof, oil, preservative, and water or buffer. Preferably, the resultant micro/nano-particulate cyclosporine or a derivative thereof has a mean particle size of less than about 3 microns. Smaller particulate cyclosporine or a derivative thereof can also be obtained, as described below.

Cyclosporine or a derivative thereof can be precipitated out from the oil droplets by adding more of the non-miscible liquid. The precipitated cyclosporine or a derivative thereof typically has a mean particle size of less than about 3 microns. If desired, the particles of cyclosporine or a derivative thereof can be prevented from aggregating or clumping together by incorporating a surfactant or emulsifier, e.g., a "surface stabilizer."

Route II is utilized for cyclosporine or a derivative thereof because it is soluble in at least one part of the emulsion base, such as the solvent, in particular, ethanol. For Route II, cyclosporine or a derivative thereof is dissolved in a mixture of oil, solvent, and surfactant to form an emulsion pre-mix. Cyclosporine or a derivative thereof remains in soluble form if preservative and water or buffer are not added to the mixture. Upon the addition of preservative, a viscosity modifier, and water or buffer and the application of shear forces, cyclosporine or a derivative thereof is precipitated into micro/nano-particles having a mean particle size of less than about 3 microns. Nanoparticles can be produced with reciprocating syringe instrumentation, continuous flow instrumentation, or high speed mixing equipment. High energy input, through high velocity homogenization or vigorous stirring, is a preferred process. The high energy processes reduce the size of the emulsion droplets, thereby exposing a large surface area to the surrounding aqueous environment. High shear processes are preferred, as low shear processes can result in larger particle sizes. This is followed by precipitation of nanoparticulate cyclosporine or a derivative thereof previously embedded in the emulsion base. The end product comprises cyclosporine or a derivative thereof in solution and particulate suspension, both distributed between the solvent, oil, preservative, and water or buffer. Nanoparticulate cyclosporine or a derivative thereof has at least one surface stabilizer associated with the surface thereof.

If desired, the water miscible oil droplets and nanoparticles of cyclosporine or a derivative thereof prepared using Route I or Route II may be filtered through either a 0.2 or 0.45 micron filter. Larger oil droplets and/or particles of cyclosporine or a derivative thereof can be created by simply increasing the water content, decreasing the oil-stabilizer-solvent content, or reducing the shear in forming the oil droplets.

For the 50× concentrated emulsion base used in Route I or Route II, the content of cyclosporine is about 0.1%-10, the content of solvent is about 0.1%-20%, the content of oil is about 5%-50%, the content of surfactant is about 0.1%-20%, the content of preservative is about 0.1%-5%, and the content of the aqueous medium is about 20%-80%, all in w/w percentage. Optionally, the viscosity modifier is present in the emulsion base in the amount of about 0.1% to about 10% (w/w). The content of each ingredient in the final product is the amount above divided by 50, with the aqueous medium being the major component, at about 98% or more.

B. Definitions

The present invention is described herein using several definitions, as set forth below and throughout the application.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The phrase "poorly water-soluble" or "water insoluble" as used herein refers to a solubility in water of less than about 30 mg/mL, less than about 20 mg/mL, less than about 10 mg/mL, less than about 1 mg/mL, less than about 0.1 mg/mL, less than about 0.01 mg/mL or less than about 0.001 mg/mL at ambient temperature and pressure and at about pH 7.

The phrase "soluble" as used herein refers to a solubility in water or another medium selected from the group consisting of greater than about 10 mg/mL, greater than about 20 mg/mL, and greater than about 30 mg/mL.

As used herein, the term "subject" is used to mean an animal, preferably a mammal, including a human or non-human. The terms "patient" and "subject" may be used interchangeably.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

As used herein, the phrase "cyclosporines and derivatives thereof" include a group of nonpolar cyclic oligopeptides with known immunosuppressant activity, as disclosed in U.S. Pat. No. 5,474,979, which is incorporated by reference in its entirety. In addition to the most common form of cyclosporine A, there are several other minor metabolites, cyclosporine B through I, identified. The present invention intends to include any individual member of the cyclosporine family, as well as a mixture of two or more members of the family, because the commercial cyclosporines may contain a mixture of several forms of cyclosporines, which all share a cyclic peptide structure consisting of eleven amino acids with a total molecular weight of about 1200. The cyclosporines and derivatives thereof also include the natural or synthetic product, as well as any substituents or different configurations of the amino acids, as long as they maintain the immunosuppressive activity and capability of enhancing or restoring the lacrimal gland tearing. The present invention further encompasses the cyclosporine A derivatives, e.g., methylthio-substituted cyclosporine A and other alkylthio-substituted cyslosporine A derivatives, as disclosed in U.S. Pat. Nos. 6,254,860 and 6,350,442, each of which is incorporated by reference in its entirety.

C. Compositions of the Invention

1. Exemplary Compositions

The methods of the invention can produce several different types of compositions. A first composition comprises: (1) microparticulate and/or nanoparticulate cyclosporine or a derivative thereof having a mean particle size of less than about 10 microns and, optionally for nanoparticulate cyclosporine or a derivative thereof, having associated with the surface thereof at least one surface stabilizer; (2) at least one preservative; (3) water or a buffer; and (4) an emulsion pre-mix or oil phase or lipophilic phase comprising at least one oil and optionally at least one solvent, and/or a viscosity modifier. The composition may additionally comprise microcrystalline cyclosporine or a derivative thereof. The particulate cyclosporine or a derivative thereof can be present in the water or buffer, oil, solvent, preservative, or a combination thereof. Such a composition is made utilizing Route I.

A second composition comprises: (1) microparticulate and/or nanoparticulate cyclosporine or a derivative thereof having a mean particle size of less than about 10 microns and, optionally for nanoparticulate cyclosporine or a derivative thereof having associated with the surface thereof at least one surface stabilizer; (2) a preservative; (3) water or a buffer; and (4) an emulsion pre-mix or oil phase or lipophilic phase comprising at least one oil, optionally at least one solvent, solubilized cyclosporine or a derivative thereof, and/or a viscosity modifier. The composition may additionally comprise microcrystalline cyclosporine or a derivative thereof. The solubilized cyclosporine or a derivative thereof may be present in oil, solvent, or a combination thereof. In addition, nanoparticulate cyclosporine or a derivative thereof can be present in the water or buffer, oil, solvent, or a combination thereof. Such a composition is made utilizing Route II.

In a further embodiment of the invention, the solubilized cyclosporine or a derivative thereof can be precipitated out from the emulsion droplets. The precipitated microparticulate cyclosporine or a derivative thereof has a mean particle size of less than about 10 microns, less than about 9 microns, less than about 8 microns, less than about 7 microns, less than about 6 microns, less than about 5 microns, less than about 4 microns, less than about 3 microns, less than about 2 microns, or about 1 micron or greater. In other embodiments of the invention, at least about 50%, at least about 60%, at least about 70%, at least about 80%, at least about 90%, at least about 95%, or at least about 99% of the particles of cyclosporine or a derivative thereof can have a diameter less than the size listed above, e.g., less than about 10 microns, less than about 9 microns, etc.

In yet another embodiments of the invention, the nanoparticles of cyclosporine or a derivative thereof have a diameter of less than about 1000 nm, less than about 900 nm, less than about 800 nm, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm. In other embodiments of the invention, at least about 50%, at least about 60%, at least about 70%, at least about 80%, at least about 90%, at least about 95%, or at least about 99% of the particles of cyclosporine or a derivative thereof can have a diameter less than the size listed above, e.g., less than about 1000 nm, less than about 900 nm, etc.

The tri-phasic compositions of the invention are beneficial for several reasons. First, formulations resulting from the Route II method comprise both solid and solubilized forms of cyclosporine or a derivative thereof. This enables a resultant pharmaceutical formulation to provide both immediate release and controlled release of the component cyclosporine or a derivative thereof, providing for fast onset of activity combined with prolonged activity of cyclosporine or a derivative thereof.

The different components of the two types of compositions described above can be separated and used independently.

2. Emulsion Globules Comprising Cyclosporine Nanoparticles and/or Solubilized Cyclosporine The emulsion globules comprising solubilized cyclosporine or a derivative thereof, nanoparticles of cyclosporine or a derivative thereof, or a combination thereof can also be isolated from the surrounding aqueous or buffer phase and used in therapeutic dosage forms. The emulsion globules can be made using food grade, USP or NF grade materials suitable for human use applications. Nanoparticulate oil globules comprising solubilized active pharmaceutical ingredient (API) and methods of making the same are described in U.S. Pat. No. 5,629,021 ("the '021 patent"), which is incorporated herein by reference. The emulsion globules of the invention typically comprise (1) solubilized cyclosporine or a derivative thereof, particulate cyclosporine or a derivative thereof, or a combination thereof; (2) at least one oil; (3) at least one solvent; (4) at least one preservative; and (5) at least one surface stabilizer or surfactant. Optionally, the emulsion globules further comprises a viscosity modifier, such as a cellulose derivative, a polysaccharide or a synthetic polymer. Emulsion globules comprising solubilized cyclosporine or a derivative thereof, particulate cyclosporine or a derivative thereof, or a combination thereof can be isolated by, for example, filtration.

In general, the emulsion globules comprising solubilized cyclosporine or a derivative thereof, nanoparticles of cyclosporine or a derivative thereof, or a combination thereof comprise a significant quantity of cyclosporine or a derivative thereof and have diameters of about 10 to about 1000 nm, with a mean a diameter of less than about 1 micron preferred, and with the smallest globules filterable through a 0.2 micron filter, such as is typically used for microbiological purification. The range of concentration of cyclosporine or a derivative thereof in the globules in the diluted final product can be from about 0.01% to about 5%. The emulsion globules can be stored at between about −20° C. and about 40° C. In one embodiment of the invention, at least about 50%, at least about 60%, at least about 70%, at least about 80%, or at least about 90% of the globules in the preparation have diameters of less than about 1 micron, less than about 900 nm, less than about 800 nm, less than about 700 nm, less than about 600 nm, less than about 500 nm, less than about 400 nm, less than about 300 nm, less than about 200 nm, or less than about 100 nm.

By varying different parameters of Route I and Route II, the size and integrity of such globules can be modified. Hence, the stability of globules comprising dissolved cyclosporine or a derivative thereof can be altered to enable the release of cyclosporine or a derivative thereof, either as a solution or precipitate. This is a microreservoir-dissolution-controlled system, where the drug solids act as depot and, as the solubilized fraction is depleted, more drug is drawn into solution form the particulate depot. Thus, the emulsion globules comprising solubilized cyclosporine or a derivative thereof enable controlled cyclosporine or a derivative thereof release over time.

In addition, the emulsion globules comprising solubilized cyclosporine or a derivative thereof, nanoparticles of cyclosporine or a derivative thereof, or a combination thereof can be diluted with aqueous solutions without stability loss. This enables the use of high concentration of cyclosporine or a derivative thereof, e.g., up to about 10%, in products which can be diluted to obtain the final product.

In a preferred embodiment, 50× concentrated cyclosporine formulation containing 2.5% w/w cyclosporine is manufactured aseptically. The particles of cyclosporine in the concentrated product have a mean particle size of less than 200 nm. Subsequently, the concentrated product is diluted with sterile PBS/saline to achieve 0.05% w/w cyclosporine in the final product, which has similar appearance to Restasis®. The final product is packaged and sealed in 0.4 ml per dose.

D. Methods of Making the Inventive Compositions

Three methods for making the compositions of the invention are described herein. One benefit of the invention is to provide methods applicable to cyclosporine or a derivative thereof, which is poorly water-soluble. Another benefit of the methods of the invention is that they do not require grinding media or specialized grinding process or equipments. The use of such grinding media can add cost and complexity to a particle size reduction process for an API. Additionally, the methods of the invention can accommodate amorphous or semi-amorphous forms of cyclosporine or a derivative thereof. In summary, the three methods are as follows: Route I: cyclosporine or a derivative thereof is insoluble or slightly soluble in any of the components of the formulation; Route II: cyclosporine or a derivative thereof is soluble or partially soluble in at least one of the components of the formulation; and Route III: cyclosporine or a derivative thereof is completely soluble in all of the components of the formulation.

1. Route I

The method of Route I essentially comprises milling cyclosporine or a derivative thereof in an emulsion base. This method requires that cyclosporine or a derivative thereof is poorly soluble or insoluble in all phases of the oil phase/lipophilic phase and the water or buffer. Hence, cyclosporine or a derivative thereof is first suspended in a mixture of a non-miscible liquid, which can comprise at least one oil, at least one solvent, at least one preservative, at least one viscosity modifier, and at least one buffer or water to form an emulsion base, followed by homogenization or vigorous stirring of the emulsion base. Nanoparticles of cyclosporine or a derivative thereof can be produced with reciprocating syringe instrumentation, continuous flow instrumentation, or high speed mixing equipment. High velocity homogenization or vigorous stirring, producing forces of high shear and cavitation, are preferred. High shear processes are preferred as low shear processes can result in larger particle sizes.

The resultant composition is a composite mixture of cyclosporine or a derivative thereof suspended in the emulsion droplet (nanoemulsion fraction of cyclosporine or a derivative thereof) and sterically stabilized microcrystalline or microparticulate cyclosporine or a derivative thereof in the media. This tri-phasic system comprises particulate cyclosporine, oil, preservative and water or buffer.

In one embodiment of the invention, the resultant microparticulate cyclosporine or a derivative thereof has a diameter of less than about 10 microns, less than about 9 microns, less than about 8 microns, less than about 7 microns, less than about 6 microns, less than about 5 microns, less than about 4 microns, less than about 3 microns, less than about 2 microns, or greater than about 1 micron.

In another embodiment of the invention, the nanoparticulate cyclosporine or a derivative thereof can have a diameter of less than about 1000 nm, less than about 900 nm, less than about 800 nm, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm.

In other embodiments of the invention, at least about 50%0, at least about 60%, at least about 70%, at least about 80%, at least about 90%, at least about 95%, or at least about 99% of the microcrystalline or microparticulate cyclosporine or a derivative thereof in a composition can have a diameter of less than about 10 microns, less than about 9 microns, less than about 8 microns, less than about 7 microns, less than about 6 microns, less than about 5 microns, less than about 4 microns, less than about 3 microns, less than about 2 microns, about 1 micron, or greater than about 1 micron and less than about 2, about 3, about 4, about 5, about 6, about 7, about 8, about 9, or about 10 microns.

In yet other embodiments of the invention, at least about 50%, at least about 60%, at least about 700%, at least about 80%, at least about 90%, at least about 95%, or at least about 99% of the nanoparticulate cyclosporine or a derivative thereof can have a diameter of less than about 1000 nm, less than about 900 nm, less than about 800 nm, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm in size.

Cyclosporine or a derivative thereof can be precipitated out from the oil droplets by adding more of the non-miscible liquid. The precipitated particles of cyclosporine or a derivative thereof typically have a diameter of less than about 10 microns, less than about 9 microns, less than about 8 microns, less than about 7 microns, less than about 6 microns, less than about 5 microns, less than about 4 microns, less than about 3 microns, less than about 2 microns, or less than about 1 micron. If desired, the particles cyclosporine or a derivative thereof can be prevented from aggregating or clumping together by incorporating a surfactant or emulsifier, e.g., a "surface stabilizer."

2. Route II and Route III

Routes II and III require that cyclosporine or a derivative thereof is soluble or partially soluble in at least one (Route II) or all of the phases (Route III) of the emulsion base; e.g., that cyclosporine or a derivative thereof is soluble in at least one oil, at least one solvent, at least one preservative, or water or buffer. In some embodiments, Route II or Ill can comprise the simultaneous milling and precipitation of cyclosporine or a derivative thereof in an emulsion base.

Route II is utilized when cyclosporine or a derivative thereof is soluble in at least one part of the emulsion base, such as the solvent, and Route III is utilized when cyclosporine or a derivative thereof is soluble in all of the components of the emulsion base, such as oil and a solvent. For Routes II and III, cyclosporine or a derivative thereof is dissolved in a mixture of oil, solvent, preservative, viscosity modifier and stabilizer to form an emulsion pre-mix. Cyclosporine or a derivative thereof remains in soluble form if water or buffer is not added to the mixture. Upon the addition of water or buffer and the application of shear forces, cyclosporine or a derivative thereof is precipitated into microparticles having a diameter of less than about 10 microns, and nanoparticles having a diameter of less than about 1 micron (as described above in Route I; the same particle sizes are applicable to Routes II and III). Nanoparticles can be produced with reciprocating syringe instrumentation, continuous flow instrumentation, or high speed mixing equipment. High energy input, through high velocity homogenization or vigorous stirring, is a preferred process. The high energy processes reduce the size of the emulsion droplets, thereby exposing a large surface area to the surrounding aqueous environment. High shear processes are preferred, as low shear processes can result in larger particle sizes.

This can be followed by precipitation of nanoparticulate cyclosporine or a derivative thereof previously embedded in the emulsion base. The end product comprises cyclosporine or a derivative thereof in solution and particulate suspension, both distributed between the solvent, oil, and water or buffer. In one embodiment, nanoparticulate cyclosporine or a derivative thereof has at least one surface stabilizer associated with the surface thereof.

If desired, the water miscible oil droplets and nanoparticles of cyclosporine or a derivative thereof prepared using Route I, Route II, or Route III may be filtered through either a 0.2 or 0.45 micron filter. Larger oil droplets and/or particles of cyclosporine or a derivative thereof can be created by simply increasing the water content, decreasing the oil-stabilizer-solvent content, or reducing the shear in forming the oil droplets.

For the 50× concentrated emulsion base used in Route I, Route II, or Route III, the content of cyclosporine is about 0.1%-10%, the content of solvent is about 0.1%-20%, the content of oil is about 5%-50%, the content of surfactant is about 0.1%-20%, the content of preservative is about 0.1%-5%, and the content of the aqueous medium is about 20%-80%, all in w/w percentage. Optionally, the viscosity modifier is present in the emulsion base in the amount of about 0.1% to about 10% (w/w). The content of each ingredient in the final product is the amount above divided by 50, with the aqueous medium being the major component, at about 98% or more.

E. Components of the Methods and Compositions of the Invention

1. Cyclosporine
a. Suitable Cyclosporine and Derivatives Thereof

The phrase "cyclosporines and derivatives thereof" is defined supra, as disclosed in U.S. Pat. Nos. 5,474,979, 6,254,860, and 6,350,442. The cyclosporines useful in the present invention include naturally occurring cyclosporines, preferably cyclosporines A, B, C, D and G, as well as synthetic and semi-synthetic cyclosporines and cyclosporine derivatives disclosed in U.S. Pat. Nos. 4,108,985, 4,210,581, 4,220,641, 4,384,996, 4,764,503, 4,703,033 and U.K. Patent Application No. 2,206,119A, which are hereby incorporated by reference in their entirety. Preferably, the cyclosporine is cyclosporine A.

b. Particle Size of Cyclosporine

As used herein, the particle size is determined on the basis of the weight average particle size as measured by conventional techniques well known to those skilled in the art, such as sedimentation field flow fractionation, laser diffraction, photon correlation spectroscopy (also known as dynamic light scattering), electroacoustic spectroscopy, or disk centrifugation.

As used herein, "nanoparticulate cyclosporine or a derivative thereof" refers to cyclosporine or a derivative thereof having a diameter of less than about 1 micron. An exemplary cyclosporine useful in the invention is cyclosporine A. "Microcrystalline cyclosporine or a derivative thereof" refers to cyclosporine or a derivative thereof having a diameter of greater than about 1 micron. In other embodiments of the invention, microparticulate cyclosporine or a derivative thereof have a diameter of less than about 10 microns, less than about 9 microns, less than about 8 microns, less than about 7 microns, less than about 6 microns, less than about 5 microns, less than about 4 microns, less than about 3 microns, less than about 2 microns, or about 1 micron or greater. In other embodiments of the invention, at least about 500, at least about 60/o, at least about 70%, at least about 80%, at least about 90%, at least about 95%, or at least about 99% of the microparticles of cyclosporine or a derivative thereof can have a diameter less than the size listed above, e.g., less than about 10 microns, less than about 9 microns, etc.

In yet other embodiments of the invention, nanoparticulate cyclosporine or a derivative thereof has a diameter of less than about 900 nm, less than about 800 nm, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm. In other embodiments of the invention, at least about 50%, at least about 60%, at least about 70%, at least about 80%, at least about 90%, at least about 95%, or at least about 99% of the nanoparticles of cyclosporine or a derivative thereof can have a diameter less than the size listed above, e.g., less than about 900 nm, less than about 800 nm, etc.

In other embodiments of the invention, at least about 60%, at least about 70%, at least about 80%, at least about 90%, at least about 95%, or at least about 99% of the particles of cyclosporine or a derivative thereof, or droplets comprising solubilized cyclosporine or a derivative thereof, have a size less than the mean particle size, less than about 3 microns, less than about 2900 nm, less than about 2800 nm, etc.

2. Oils

For both the methods of Route I and Route II and the compositions of the invention, any suitable oil can be used. Exemplary oils that can be used include, for example, vegetable oils, nut oils, fish oils, lard oil, mineral oils, squalane, tricaprylin, and mixtures thereof. Specific examples of oils that may be used include, but are not limited to, almond oil (sweet), apricot seed oil, borage oil, canola oil, coconut oil, corn oil, cotton seed oil, fish oil, jojoba bean oil, lard oil, linseed oil (boiled), Macadamia nut oil, medium chain triglycerides, mineral oil, olive oil, peanut oil, safflower oil, sesame oil, soybean oil, squalene, sunflower seed oil, tricaprylin (1,2,3-trioctanoyl glycerol), wheat germ oil, and mixtures thereof.

3. Stabilizers or Surfactants

The stabilizer used in the methods and compositions of the invention associates with, or adsorbs, to the surface of the nanoparticulate cyclosporine or a derivative thereof, but does not covalently bind to cyclosporine or a derivative thereof. In addition, the individual stabilizer molecules are preferably free of cross-linkages. The stabilizer is preferably soluble in water. One or more stabilizers may be used in the compositions and methods of the invention. As used herein, the terms "stabilizer", "surface stabilizer", and "surfactant" are used interchangeably.

Any suitable nonionic or ionic surfactant may be utilized in the compositions of the invention, including anionic, cationic, and zwitterionic surfactants. Exemplary stabilizers or surfactants that may be used in both Routes I and II include, but are not limited to, non-phospholipid surfactants, such as the Tween (polyoxyethylene derivatives of sorbitan fatty acid esters) family of surfactants (e.g., Tween 20, Tween 60, and Tween 80), nonphenol polyethylene glycol ethers, sorbitan esters (such as Span and Arlacel), glycerol esters (such as glycerin monostearate), polyethylene glycol esters (such as polyethylene glycol stearate), block polymers (such as Pluronics-), acrylic polymers (such as Pemulen®), ethoxylated fatty esters (such as Cremophor® RH-40), ethoxylated alcohols (such as Brij®), ethoxylated fatty acids, monoglycerides, silicon based surfactants, polysorbates, Tergitol NP-40 (Poly(oxy-1,2-ethanediyl), α-(4-nonylphenol)-.omega.-hydroxy, branched [molecular weight average 1980]), and Tergitol NP-70 (a mixed surfactant—AQ=70%).

4. Solvents

Any suitable solvent can be used in the methods and compositions of the invention. Exemplary solvents include, but are not limited, to isopropyl myristate, triacetin, N-methyl pyrrolidinone, aliphatic or aromatic alcohols, polyethylene glycols, propylene glycol. An example of an alcohol useful in the present invention includes, but is not limited to ethanol. Other short chain alcohols and/or amides may be used. Other solvents include dimethyl sulfoxide, dimethyl acetamide, and ethoxydiglycol. Mixtures of solvents can also be used in the compositions and methods of the invention.

5. Water or Buffer

If the methods and/or compositions of the invention use or comprise water or a buffer, the aqueous solution is preferably a physiologically compatible solution such as water or phosphate buffered saline.

6. Preservatives

The formulations of the invention have anti-microbial properties. The anti-microbial properties can be associated with the formulation. As an example, the formulations described herein, in the absence of cyclosporine, can exhibit antimicrobial activity.

Antimicrobial agents or preservatives are added to non-sterile dosage forms to protect them from microbiological growth or from microorganisms that are introduced inadvertently during or subsequent to the manufacturing process. In the case of sterile articles used in multi-dose containers, antimicrobial preservatives are added to inhibit the growth of microorganisms that may be introduced by repeatedly withdrawing individual doses.

U.S. Food and Drug Administration guidelines require that antimicrobial effectiveness, whether inherent in the product (e.g., for an antibiotic agent) or whether produced because of the addition of an antimicrobial agent, must be demonstrated for all injections packaged in multiple-dose containers or for other products containing antimicrobial preservatives. Antimicrobial effectiveness must be demonstrated for multiple-dose topical and oral dosage forms, and for other dosage forms such as ophthalmic, otic, nasal, irrigation, and dialysis fluids. See USP 25, Section 51, "Antimicrobial Effectiveness Testing."

The formulations of the invention meet the Antimicrobial Effectiveness Test as described in the United States Pharmacopeia (USP—General Chapter #51). The standard USP testing requires evaluation in five microorganisms: *Aspergillus niger* (ATCC 16404), *Candida albicans* (ATCC 10231), *Escherichia coli* (ATCC 8739), *Pseudomonas aeruginosa* (ATCC 9027) and *Staphylococcus aureus* (ATCC 6538).

The formulations of the invention comprise preservatives, e.g., water soluble quaternary ammonium compounds, such as cetyltrimethylammonium bromide, cetylpyridinium chloride, benzethonium chloride, and benzalkonium chloride. Preferably, the preservative is benzalkonium chloride.

BKC has been used as a preservative in ophthalmic formulations for many years. The formulation of the present invention contains BKC at a concentration that is recognized to be sufficient to qualify the USP Preservative Efficacy testing. There is sufficient literature evidence available to prove preservative efficacy for BKC used in ophthalmic formulations (Handbook of Pharmaceutical Excipients, $3^{rd}$ edition (2000), edited by Arthur H. Kibbe, published by American Pharmaceutical Association and Pharmaceutical Press, pp. 33-35). Hence, the formulation of the invention is suitable for multi-dose packaging.

In the present invention, BKC unexpectedly functions as a cationic agent, which contributes to the prolonged drug residence time. This property of the compositions of the invention enable fewer applications of the dosage form to the eye, which is generally preferred by patient populations. Moreover, the dosage applied is more effective, as the cationic property of the dosage form results in the drug "adhering" to the eye, rather than having much of the dosage form run out of the eyes following administration.

It is believed that the beneficial aspects of the novel opthalmic cyclosporine compositions of the invention result from a synergistic combination of: (1) particle size of cyclosporine; (2) potential presence of cyclosporine in both a solubilized and particulate form in the dosage; (3) the cationic property of the dosage form, and (4) the stable, non-irritating final product suitable for multi-dose packaging.

In general, tissues in the body are considered to be negatively charged. As a result, a positively-charged (cationic) product is considered to have better chance of improved interaction of the product with the tissue. This improved interaction between the cationic product and body tissues is not always observed, however.

Prior art describes that for a biphasic system, oil-soluble cationic lipids, e.g., stearylamine, has been used to impart a net positive charge onto oil droplet, whereby the droplet being electrostatically attracted to the anionic surface of the eye. See, for example, U.S. Pat. No. 6,656,460.

When water-soluble, quaternary ammonium compounds are used, they will not impart positive charge on the emulsion. Instead, they are likely to be adsorbed or loosely bound onto the surface and may result in a charge. Typically, when quaternary ammonium compounds are used, the acidic pH needs to be maintained for protonation of the groups to impart positive charge. In the present invention, it is unexpectedly found that BKC induces positive charge, under about neutral pH, in a multi-phasic composition having a solid particulate phase and an oil phase dispersed in aqueous milieu. Surprisingly, the cationic emulsion prepared using BKC shows significantly prolonged residence time in the eye using human cornea mounted on a Franz cell.

Due to the presence of the preservative, the formulations of the present invention can be packaged into multi-dose containers. Moreover, as demonstrated in the following working examples, the presence of cyclosporine was only detected locally and administration of the formulations of the invention does not cause any irritation to the eye. Hence, the formulations of the invention are suitable for daily application.

7. Viscosity Modifier

The ophthalmic formulation may further comprise a viscosity modifier, such as a cellulose derivative, a polysaccharide or a synthetic polymer. The viscosity of the formulations of the present invention can be increased without compromising other properties.

The following examples are given to illustrate the present invention. It should be understood, however, that the invention is not to be limited to the specific conditions or details described in these examples. Throughout the specification, any and all references to a publicly available document, including U.S. patents, are specifically incorporated by reference.

Example 1

The purpose of this example was to prepare formulations according to the invention comprising cyclosporine and a cationic preservative, benzalkonium chloride.

The commercial Restasis® standard, which contains cyclosporine A (0.05% w/w) and inactive ingredients like glycerin, castor oil, polysorbate 80, carbomer 1342, purified water and sodium hydroxide, was used as a control for the purpose of comparing the properties of the formulation.

Cyclosporine is commercially available under the trade names SANDIMMUNE® and NEORAL®. It is a cyclic polypeptide immunosuppressant agent consisting of 11 amino acids. It is produced as a metabolite by the fungus species Beauveria nlyea. Chemically, cyclosporine is designated as [R—[R*,R*-(E)]]-cyclic(L-alanyl-D-alanyl-N-methyl-L-leucyl-N-methyl-L-leucyl-N-methyl-L-valyl-3-hydroxy-N, 4-dimethyl-L-2-amino-6-octenoyl-L-α-aminobutyryl-N-methylglycyl-N-methyl-L-leucyl-L-valyl-N-methyl-L-leucyl). The chemical structure of cyclosporine (also known as cyclosporin A) is:

Cyclosporine was dissolved in ethanol at room temperature. Polysorbate 80 and crodamol (Table 1) were then added to the cyclosporine solution and mixed well with a paddle stirrer. Then benzalkonium chloride solution and water were added and mixing was continued for about 5 minutes. The coarse emulsion was then fed into a high pressure homogenizer (APV Invensys, model APV-1000) and homogenized at 10,000 psi for three passes. The resultant 50× concentrated composition, described below in Table 1, comprised cyclosporine dissolved in the solvent ethanol and nanoparticulate cyclosporine particles associated with the surface stabilizer polysorbate 80 present in the water portion of the emulsion. The concentrated emulsion was collected and diluted with phosphate buffered saline (PBS), pH 7.2, at the ratio of 1 part of concentrated emulsion with 49 parts of PBS to obtain the final product, cationic micellar nanoparticle formulation (cMNP) of cyclosporine. The cMNP and Restasis® have similar appearance as milky white emulsion. The viscosity of the formulation of the invention can be increased without compromising other properties.

Figure 1A:
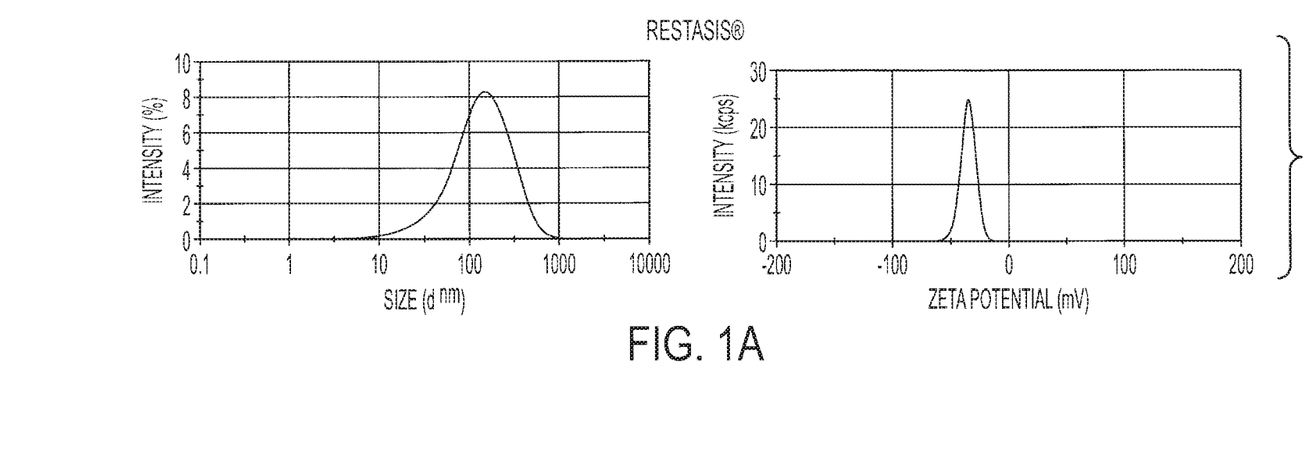
FIGS. 1A, 1B, and 1C show mean particle size and mean zeta potential for Restasis®, for the cationic micellar nanoparticle (cMNP) formulation of cyclosporine A prepared according to Example 1, and for the neutral micellar nanoparticle (nMNP) formulation prepared according to Example 2, respectively.
Figure 1B:
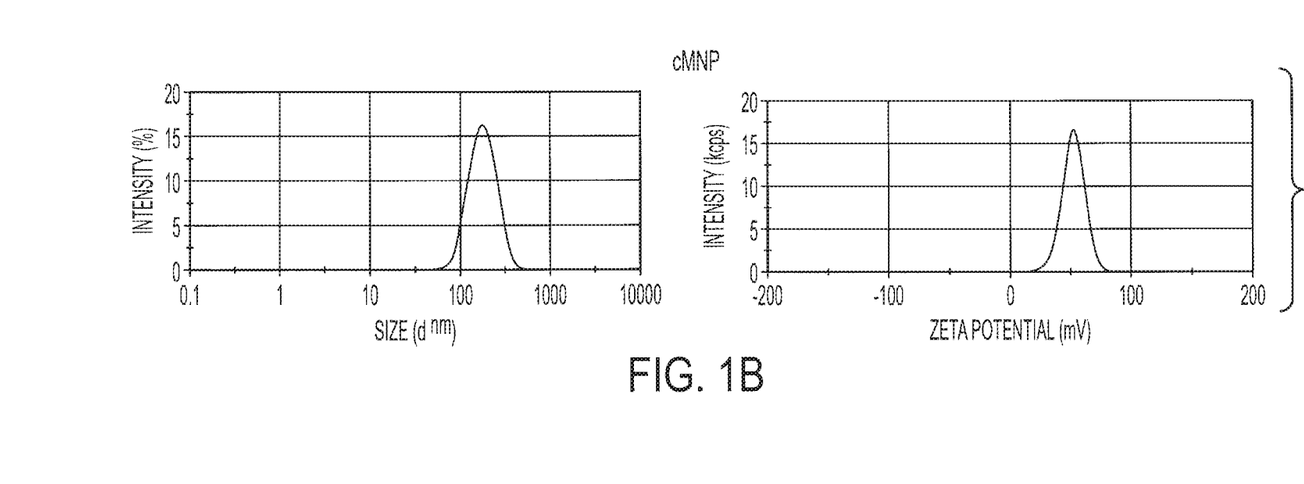

The resultant particle size and zeta potential of cMNP of cyclosporine were measured and compared with those of the commercial Restasis® standard, as shown in FIGS. 1A and 1B, as well as in Table 2.

TABLE 1

| Ingredient | % w/w in 50X cMNP | % w/w in 1X final cMNP product |
|---|---|---|
| Cyclosporine | 2.5 | 0.05 |
| Ethanol | 5.0 | 0.1 |
| Polysorbate 80 | 5.0 | 0.1 |
| Medium chain triglycerides (Crodamol GTCC) | 45.0 | 0.9 |
| Benzalkonium chloride | 1.25 | 0.025 |
| Water | 41.25 | 98.825 |

TABLE 2

| Properties | Restasis ® | cMNP |
|---|---|---|
| pH | 6.5-8.0 | 7.23 |
| Osmolality | 230-320 mOsm/Kg | 308 mOsm/Kg |
| Mean particle size | 113 nm | 167 nm |
| Viscosity | — | 0.89 mPa · s |
| Mean zeta potential | −35.0 mV | +51.3 mV |

Example 2

The purpose of this example was to prepare formulations comprising cyclosporine and a permeation enhancer, vitamin E TPGS. The formulations of this example are used as a comparison to the formulations of the invention prepared according to Example 1.

Cyclosporine and Restasis® standard are the same as those in Example 1. Vitamin E TPGS (d-alpha-tocopheryl polyethylene glycol-1000 succinate, obtained from Eastman Chemical Company) is a water-soluble form of natural-source vitamin E.

Cyclosporine was dissolved in ethanol at room temperature. Polysorbate 80 and crodamol (Table 3) were then added to the cyclosporine solution and mixed well with a paddle stirrer. Then vitamin E TPGS solution and water were added and mixing was continued for about 5 minutes. The coarse emulsion was then fed into a high pressure homogenizer (APV Invensys, model APV-1000) and homogenized at 10,000 psi for three passes. The resultant 50× concentrated composition, described in Table 3, comprised cyclosporine dissolved in the solvent ethanol and nanoparticulate cyclosporine particles associated with the surface stabilizer polysorbate 80 present in the water portion of the emulsion. The concentrated emulsion was collected and diluted with phosphate buffered saline (PBS), pH 7.2, at the ratio of 1 part of concentrated emulsion with 49 parts of PBS to obtain the final product, neutral micellar nanoparticle formulation (nMNP) of cyclosporine. The nMNP and Restasis® have similar appearance as milky while emulsion. The viscosity of the formulation of the invention can be increased without compromising other properties.

Figure 1C:
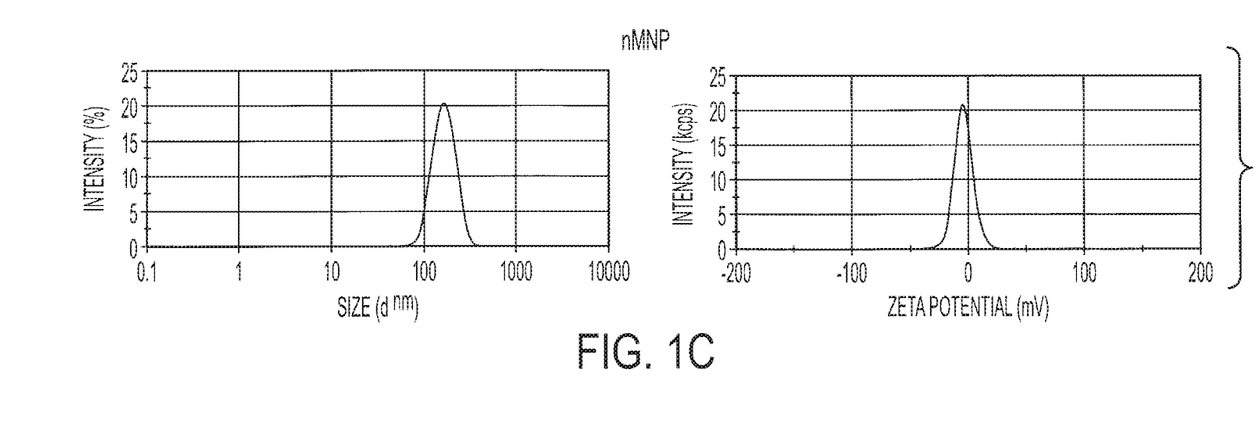

The resultant particle size and zeta potential of nMNP of cyclosporine were measured and compared with those of the commercial Restasis® standard, as shown in FIGS. 1A and 1C, as well as in Table 4.

TABLE 3

| Ingredient | % w/w in 50X nMNP | % w/w in 1X final nMNP product |
|---|---|---|
| Cyclosporine | 2.5 | 0.05 |
| Ethanol | 5.0 | 0.1 |
| Polysorbate 80 | 5.0 | 0.1 |
| Medium chain triglycerides (Crodamol GTCC) | 45.0 | 0.9 |
| Vitamin E TPGS | 1.25 | 0.025 |
| Water | 41.25 | 98.825 |

TABLE 4

| Properties | Restasis ® | nMNP |
|---|---|---|
| pH | 6.5-8.0 | 5.24 |
| Osmolality | 230-320 mOsm/Kg | 311 mOsm/Kg |
| Mean particle size | 113 nm | 154 nm |
| Viscosity | — | 0.87 mPa · s |
| Mean zeta potential | −35.0 mV | −4.15 mV |

Example 3

The purpose of this example was to test the formulations prepared in Example 1 and Example 2 for drug residence on cornea, for possibility of once-daily application, and for systemic absorption, using an in vitro Franz cell-human cornea assembly.

The protocol is as follows: isolated human cornea was obtained from an eye bank. The corneas were collected from donors and refrigerated in a suitable preservation medium. The preserved cornea was allowed to reach room temperature for about 20 minutes, and then rinsed with PBS to remove the preservation medium. The corneas were mounted horizontally between the donor and receptor halves of the Franz diffusion cells. The surface area of the cornea exposed to the formulation in the donor chamber is 0.64 $cm^2$, and the receptor cell volume was 5.0 ml. The receptor compartment was filled with 0.01M PBS, pH 7.4, and ethanol at a ratio of 9:1. A double water circulation jacket at 37° C. surrounds the receptor cell in order to have the cornea temperature maintained at physiologic level. The cMNP and nMNP formulations prepared according to Example 1 and Example 2, as well as the Restasis® standard, were applied over the surface of the cornea gravimetrically using a syringe. Periodic samples of 1.0 ml each were taken from the receptor cell to measure the amount of drug transporting across the cornea at time points of 0, 2, 4, 8, and 24 hours, respectively. At each time point, the donor sample was discarded and fresh donor sample was replenished. At the end of 24 hours, the cornea were collected, washed and homogenized in PBS:ethanol (9:1) and assayed for drug residence.

Figure 2:
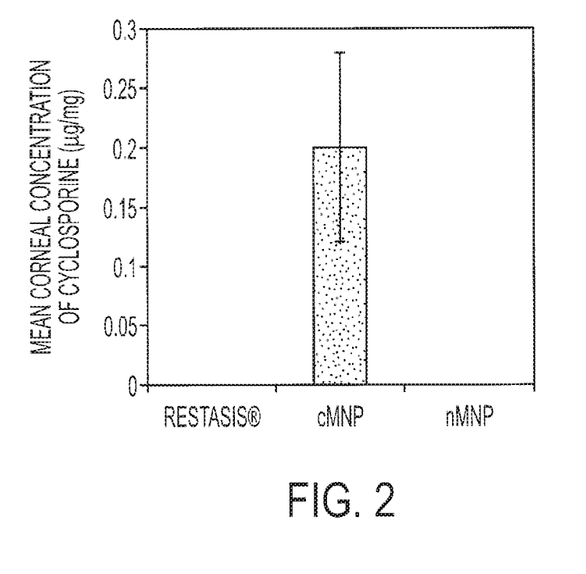
FIG. 2 shows the mean corneal concentration of cyclosporine in a Franz cell-human cornea model. High level of cyclosporine was detected in the cornea for the cMNP formulation, but not for the nMNP formulation or Restasis®.

No drug presence in the receptor compartment was detected at any time point. Hence, both formulations are suitable for once-daily application and the systemic availability of cyclosporine for both formulations is expected to be at comparable level to that of Restasis®. Moreover, FIG. 2 illustrates that significantly high level of cyclosporine was retained in the cornea for the cMNP formulation prepared according to Example 1. Therefore, the cMNP formulation is expected to have a longer retention within the cul-de-sac via electrostatic attraction with ocular tissue.

Example 4

The purpose of this example was to test the formulations prepared in Example 1 and Example 2 for biocompatibility.

To determine the in vivo irritant and/or corrosive effects, the cMNP and nMNP formulations prepared according to Example 1 and Example 2 were instilled into the rabbit eye upon once-a-day application for 7 consecutive days.

Six healthy New Zealand White rabbits were assigned to two groups of three animals per group. One group was dosed with the cMNP formulation, while the other was dosed with the nMNP formulation. All animals were dosed daily for seven consecutive days with 0.1 ml of the formulation into the conjunctival sac of the left eye of each rabbit. The right eye served as the untreated control. The treated eyes were examined for irritation using the Draize technique, pretest, prior to each subsequent dose and at the time points of 24, 48 and 72 hours, respectively, following the final dose. Observations for mortality, toxicity and pharmacologic effects were made prior to each ocular observation period. Body weights were recorded pretest. The animals were humanely sacrificed using $CO_2$, following the final observation.

The results show that there was no evidence of ocular irritation noted in any eye dosed with either the cMNP or the nMNP formulation and that there were no abnormal physical signs noted during the study. Hence, both the cMNP and the nMNP formulations are well-tolerated.

Example 5

The purpose of this example was to test the formulations prepared in Example 1 and Example 2 for stability.

Figure 3:
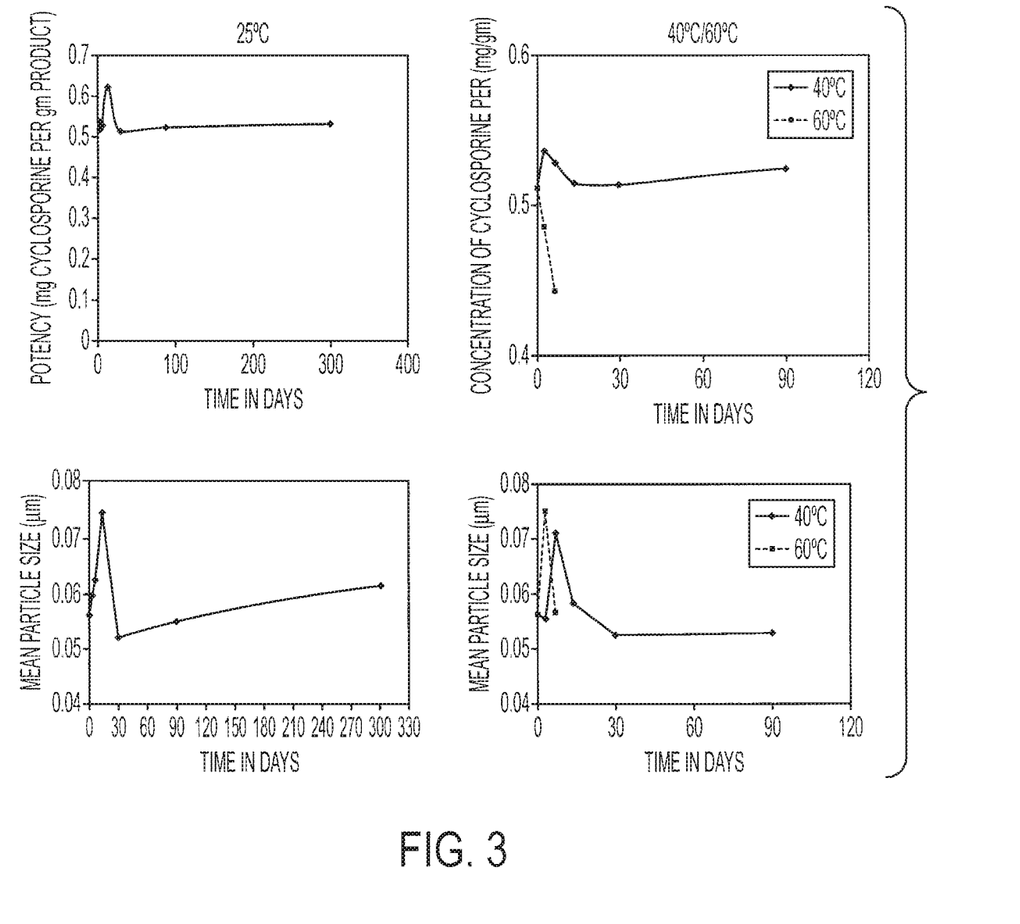
FIG. 3 depicts the stability data for the cMNP formulation stored at 25° C., 40° C. and 60° C., respectively, in terms of cyclosporine potency and mean particle size.
Figure 4:
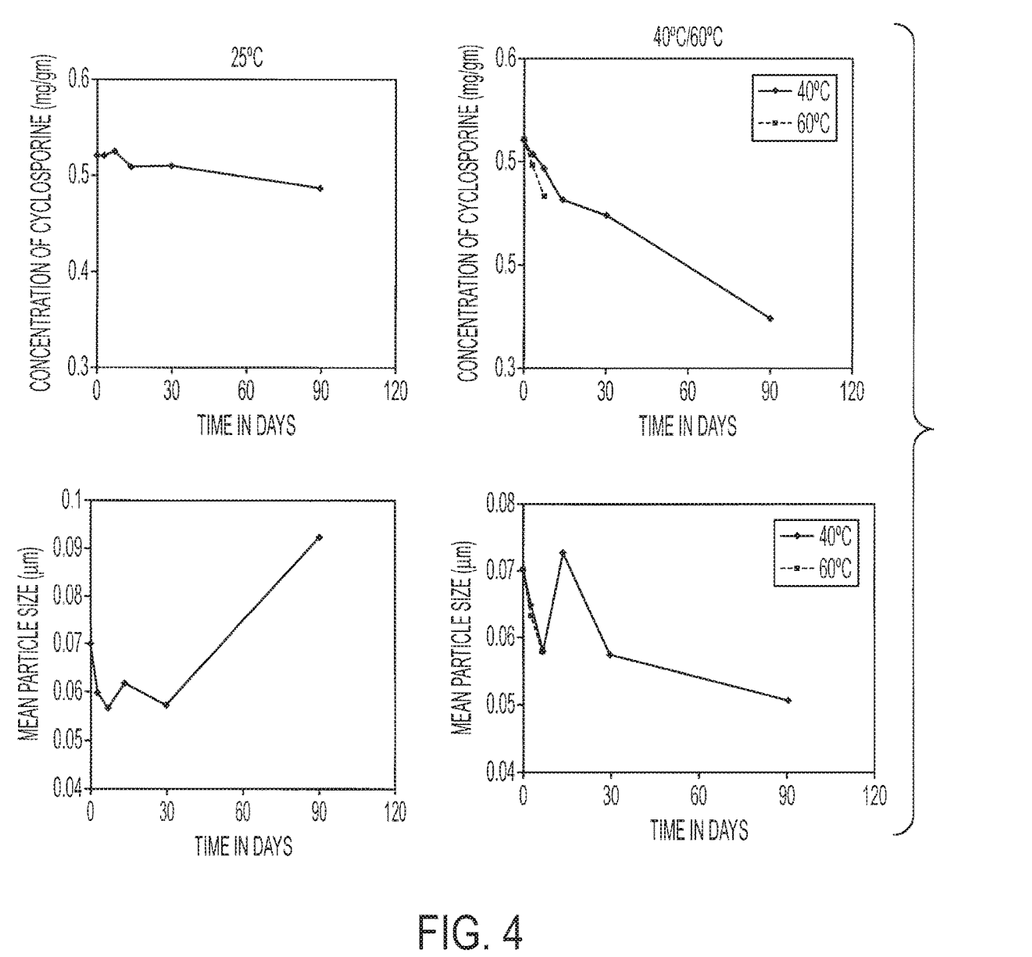
FIG. 4 depicts the stability data for the nMNP formulation stored at 25° C., 40° C. and 60° C., respectively, in terms of cyclosporine potency and mean particle size.

Both formulations were subjected to an in-house or informal non-ICH stability study. The storage temperatures and time points taken for the stability test are as follows:
1. 25° C.: 0, 1, 2, 4, 12, and 40 weeks;
2. 40° C.: 1, 2, 4 and 12 weeks;
3. 60° C.: 1 week The stability data, in terms of the potency of cyclosporine and the mean particle size, is depicted in FIG. 3 and FIG. 4, for the cMNP formulation and the nMNP formulation, respectively. For the cMNP formulation, the results show that there was no change in physical appearance of the emulsion for any storage condition at any time point tested. pH was stable at 7.3±0.3 across all storage conditions and time pointes tested. The cyclosporine content dropped by approximately 10/o for 60° C. storage condition at 1-week time point. However, the 25° C. and 40° C. storage conditions did not cause any significant decrease in potency during the test period. The mean particle size did not change during the test period for any storage condition tested. Hence, the cMNP formulation of cyclosporine will likely be stable for two years at room temperature. FIG. 4 shows that the nMNP formulation is stable for up to 12 weeks at 25° C. or at 40° C.

Example 6

The purpose of this example was to manufacture the cyclosporine formulation.

50× concentrated cyclosporine formulation containing 2.5% w/w cyclosporine is manufactured aseptically according to the description in Example 1 or Example 2. The particles of cyclosporine in the concentrated product have a mean particle size of less than 200 nm. Subsequently, the concentrated composition is diluted with sterile PBS/saline to achieve 0.05% w/w cyclosporine in the final product, which has similar appearance to Restasis®. The final product is packaged and sealed in 0.4 ml per dose.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A method of treating dry eye in a subject in need thereof, comprising administering to the eye of a subject with dry eye a nanoemulsion formulation of a cyclosporine comprising:
   (a) about 0.002% to about 0.2% w/w of a cyclosporine selected from the group consisting of cyclosporines A, B, C, D, and G as the only active pharmaceutical ingredient;
   (b) about 0.002% to about 0.4% w/w of ethanol
   (c) about 0.1% to about 1.0% w/w of at least one oil, wherein the at least one oil comprises a medium chain triglyceride;
   (d) about 0.002% to about 0.4% w/w of at least one surfactant; and
   (e) an aqueous phase;
wherein the cyclosporine is present at least (i) dissolved in globules of the at least one oil and (ii) as solid nanoparticles suspended in the aqueous phase.

2. The method of claim 1, wherein the surfactant is a polysorbate.

3. The method of claim 1, wherein the aqueous phase is water or phosphate buffered saline.

4. The method of claim 1, wherein the globules of the at least one oil and the solid nanoparticles each have a mean diameter between about 100 and about 500 nm.

5. The method of claim 1, wherein administration of the nanoemulsion formulation of cyclosporine results in a higher concentration of cyclosporine in the cornea as compared to administering the same dosage of cyclosporine in the absence of a nanoemulsion formulation.

6. The method of claim 1, wherein administration of the nanoemulsion formulation of cyclosporine results in a higher binding of cyclosporine to the cornea as compared to administering the same dosage of cyclosporine in the absence of a nanoemulsion formulation.

7. The method of claim 1, wherein the nanoemulsion formulation is phospholipid-free.

8. The method of claim 1, wherein:
   (a) the cyclosporine is cyclosporine A; and
   (b) the surfactant is a polysorbate.

9. The method of claim 1, wherein the nanoemulsion formulation further comprises a cellulose derivative.

10. The method of claim 1, wherein the nanoemulsion formulation further comprises a polysaccharide.

11. The method of claim 1, wherein the cyclosporine is cyclosporine A.

12. The method of claim 1, wherein the nanoemulsion formulation administered to the eye of the subject further comprises a preservative.

13. The method of claim 12, wherein the preservative is selected from the group consisting of cetyltrimethylammonium bromide, cetylpyridinium chloride, benzethonium chloride, and benzalkonium chloride.

14. The method of claim 12, wherein the aqueous phase is water or phosphate buffered saline.

15. The method of claim 12, wherein the nanoemulsion formulation is phospholipid-free.

16. The method of claim 12, wherein the globules of the at least one oil and the solid nanoparticles each have a mean diameter between about 100 and about 500 nm.

17. The method of claim 1, wherein the globules of the at least one oil and the solid nanoparticles each have a mean diameter between about 100 and about 250 nm.

18. The method of claim 1, wherein the cyclosporine is at a concentration of about 0.05% w/w.

19. The method of claim 1, wherein the aqueous phase is at a concentration of at least about 98% w/w.

20. The method of claim 8, wherein the cyclosporine is at a concentration of about 0.05% w/w.

21. The method of claim 8, wherein the aqueous phase is at a concentration of at least about 98% w/w.

* * * * *